(12) United States Patent
Schuhrke et al.

(10) Patent No.: US 8,308,298 B2
(45) Date of Patent: Nov. 13, 2012

(54) MICROSCOPY SYSTEM FOR EYE SURGERY

(75) Inventors: Thomas Schuhrke, Munich (DE);
Günter Meckes, Munich (DE); Stefan Gräber, Munich (DE); Keith Thornton, Puchheim (DE)

(73) Assignee: Carl Zeiss Meditec AG, Jena (DE)

( * ) Notice: Subject to any disclaimer, the term of this patent is extended or adjusted under 35 U.S.C. 154(b) by 65 days.

(21) Appl. No.: 12/801,780

(22) Filed: Jun. 24, 2010

(65) Prior Publication Data

US 2011/0019151 A1    Jan. 27, 2011

Related U.S. Application Data

(63) Continuation-in-part of application No. 12/801,689, filed on Jun. 21, 2010.

(60) Provisional application No. 61/213,608, filed on Jun. 24, 2009.

(51) Int. Cl.
*A61B 3/14* (2006.01)
*A61B 3/00* (2006.01)

(52) U.S. Cl. ........... 351/206; 351/246
(58) Field of Classification Search ........... 351/200–246
See application file for complete search history.

(56) References Cited

U.S. PATENT DOCUMENTS

| | | | |
|---|---|---|---|
| 5,070,883 A | 12/1991 | Kasahara |
| 6,030,080 A | 2/2000 | Oehman |
| 6,204,858 B1 | 3/2001 | Gupta |
| 6,254,046 B1 | 7/2001 | Biber |
| 6,322,216 B1 | 11/2001 | Yee et al. |
| 6,556,853 B1 | 4/2003 | Cabib et al. |
| 6,830,334 B2 | 12/2004 | Niven et al. |
| 7,044,602 B2 | 5/2006 | Chernyak |
| 7,261,415 B2 | 8/2007 | Chernyak |
| 7,284,858 B2 | 10/2007 | Bergner et al. |

(Continued)

FOREIGN PATENT DOCUMENTS

DE    102 97 574 T5    4/2005

(Continued)

OTHER PUBLICATIONS

Daugman, J., "How Iris Recognition Works", IEEE Transactions on Circuits and Systems for Video Technology, vol. 14, No. 1, 2004, pp. 21 to 30.

(Continued)

*Primary Examiner* — Mohammed Hasan
(74) *Attorney, Agent, or Firm* — Walter Ottesen

(57) ABSTRACT

The invention relates to an eye surgery microscopy system (1) having an imaging optic (14, 11) for the generation of the image of an object plane (15) and having an electronic image sensor (22), which detects the image of the object plane (15) and is connected to a computer unit (5) for the computation of the position of the center of a circular structure (44) of a patient eye (16). The computer unit (5) is designed for the computation of the position of a patient eye (16) outside of the center (52) of the circular structure (44) and provided with at least one marking (46, 48). The computer unit (5) determines the position of the at least one marking (46, 48) with reference to the computed center (52) by means of image processing via correlation with a comparison information, and an angular position of the at least one marking (46, 48) with reference to the computed center (52) by means of image processing.

33 Claims, 7 Drawing Sheets

U.S. PATENT DOCUMENTS

| | | |
|---|---|---|
| 7,467,869 B2 | 12/2008 | Kahlen |
| 7,699,468 B2 | 4/2010 | Gaida |
| 2003/0108225 A1* | 6/2003 | Li .................................. 382/118 |
| 2003/0181803 A1 | 9/2003 | Sander |
| 2004/0102799 A1 | 5/2004 | Perez et al. |
| 2004/0143244 A1 | 7/2004 | Gray et al. |
| 2005/0110947 A1* | 5/2005 | Chaduc ........................ 351/206 |
| 2006/0044509 A1 | 3/2006 | Fluegge et al. |
| 2006/0116668 A1 | 6/2006 | Gray et al. |
| 2006/0228011 A1 | 10/2006 | Everett et al. |
| 2006/0247659 A1 | 11/2006 | Moeller et al. |
| 2007/0171363 A1 | 7/2007 | Chen et al. |
| 2008/0252849 A1 | 10/2008 | Van Saarloos |

FOREIGN PATENT DOCUMENTS

| | | |
|---|---|---|
| DE | 20 2005 019 715 U1 | 2/2006 |
| DE | 20 2005 021 156 U1 | 4/2007 |
| DE | 10 2005 055 058 A1 | 5/2007 |
| DE | 600 30 995 T2 | 6/2007 |
| DE | 10 2007 055 919 A1 | 6/2009 |
| DE | 10 2007 055 921 A1 | 6/2009 |
| DE | 10 2007 055 922 A1 | 6/2009 |
| DE | 10 2007 055 923 A1 | 6/2009 |
| DE | 10 2007 055 924 A1 | 6/2009 |
| WO | WO 2007/085682 | 8/2007 |
| WO | WO 2009/080789 A1 | 7/2009 |
| WO | WO 2009/080790 A1 | 7/2009 |
| WO | WO 2009/080791 A1 | 7/2009 |
| WO | WO 2009/080792 A1 | 7/2009 |
| WO | WO 2009/080793 A1 | 7/2009 |

OTHER PUBLICATIONS

Heishman, R. et al, "PUPILS—Enabling a Dialogue Between the Machine and the Brain", IEEE, 2001, pp. 87 to 93.

Ivins, J. et al, "A deformable model of the human iris for measuring small three-dimensional eye movements", Machine Vision and Applications (1998) 11: pp. 42 to 51.

Leimberg, D. et al, "Heuristics for speeding up gaze estimation", XP-008063327.

Newman, R. et al, "Real-Time Stereo Tracking for Head Pose and Gaze Estimation", IEEE, 2000, pp. 122 to 128.

Perez, C. et al, "Log-Linear Elliptic Transform for Frontal-Face Parameter Estimation", IEEE, 2007, pp. 1130 to 1134.

Smolka, B. et al, "Towards automatic redeye effect removal", Pattern Recognition Letters 24 (2003), pp. 1767 to 1785, Elsevier Science B.V.

Song, J. et al, "A robust eye detection method using combined binary edge and intensity information", Pattern Recognition 39 (2006), pp. 1110 to 1125, Elsevier Ltd.

Toennies, K. et al, "Feasibility of Hough-Transform-Based Iris Localisation for Real-Time-Application", IEEE, 2002, pp. 1053 to 1058.

Yuille, A. et al, "Feature Extraction from Faces Using Deformable Templates", International Journal of Computer Vision, 1992, 8:2, pp. 99 to 111.

* cited by examiner

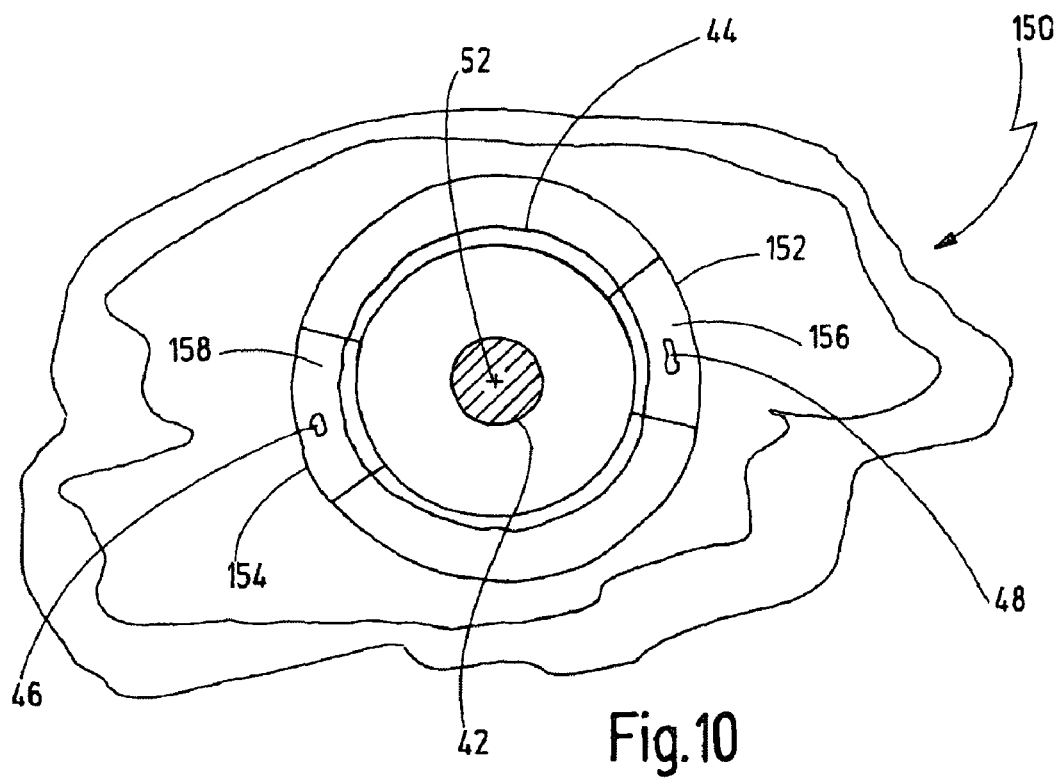
Fig.10
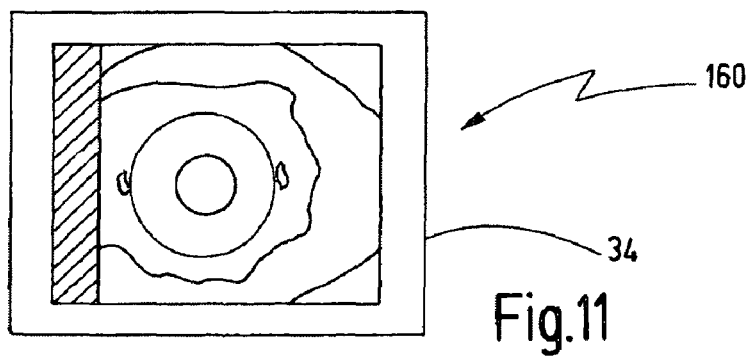
Fig.11
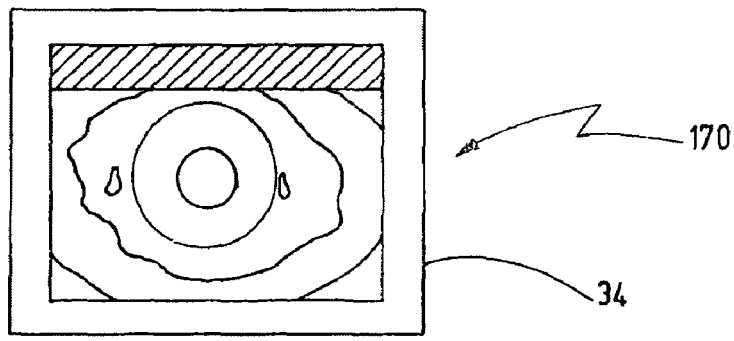

MICROSCOPY SYSTEM FOR EYE SURGERY

CROSS REFERENCE TO RELATED APPLICATIONS

This application is a continuation-in-part application of U.S. patent application Ser. No. 12/801,689, filed Jun. 21, 2010, publication 2011/0019150 A1, published Jan. 27, 2011, and claims priority of U.S. provisional application Ser. No. 61/213,608, filed Jun. 24, 2009, and the entire contents of both of the above applications are incorporated herein by reference.

FIELD OF THE INVENTION

The invention relates to an eye surgery microscopy system having an imaging optic for generating the image of an object plane and having an electronic image sensor detecting the image of the object plane. The sensor is connected to a computer unit for computing the position of the center of the circular structure of a patient eye.

BACKGROUND OF THE INVENTION

An eye surgery microscopy system is required for cataract surgery. The eye surgery microscopy system is used here for magnifying visualization of the surgical region. During the cataract surgery, the natural lens of a patient eye in which a cataract has developed is replaced with an artificial lens, a so-called intraocular lens. An opening in the lens capsule is prepared via an incision through the sclera or cornea within the inner edge of the iris. The natural lens is then smashed through this opening with an ultrasound device and later removed. After the removal of the natural lens, the intraocular lens is introduced through the opening in the lens capsule of the patient eye.

An eye surgery microscopy system of the type referred to above is known from US 2006/0247659 A1. There, an ophthalmologic surgical microscope is described which has a pattern generator. With the pattern generator, a marking pattern can be superposed onto the viewed image in the surgical microscope which serves as an orientation aid during surgery on a patient eye, for example, in the so-called cataract surgery. The pattern generator is connected to a unit for the determination of the pupil position of the patient eye and this unit has an image sensor with a computer unit.

In eye surgery, intraocular lenses having spherical, aspherical, multifocal and even toric geometries are used.

In toric intraocular lenses, it is necessary that the axis of the torus of the intraocular lens is aligned in a defined manner in the patient eye during the cataract surgery to compensate for vision defects of the patient.

It is known to apply in advance of the surgery on the patient eye, as a rule, two mutually opposite dot-shaped markings at the edge of the limbus with a tincture tolerated by the patient. These markings serve as a reference for the surgeon. During surgery, a video image of the patient is generated on which these markings are visible. After introducing the toric intraocular lens into the patient eye, the toric intraocular lens is aligned while using a template guided on the image screen. This template is moved by an assistant in front of the display screen corresponding to markings which are visible on the video image of the patient eye.

It is further known, in addition to applying reference markings to the patient eye, to additionally prepare on the patient eye also a marking for the target position of the toric intraocular lens. This, however, makes an additional marking step necessary.

The image of the object region, which a surgeon sees in a cataract surgery, is not stationary. On the one hand, the patient eye can shift during surgery, notwithstanding a local anesthesia. On the other hand, mechanical vibrations of eye surgery microscopy systems cannot be completely prevented. The microscopy systems are, as a rule, held with an adjustable stand unit above the head of the patient undergoing surgery. These vibrations become disturbingly noticeable during the imaging of an object region and primarily at higher magnifications. A highly movable image of the object region makes an alignment of a toric intraocular lens especially difficult when using a template guided in front of the video display screen.

SUMMARY OF THE INVENTION

The task of the invention is to provide an eye surgery microscopy system which enables the automatic display of the position and orientation for a toric intraocular lens in a patient eye provided with a reference marking to the surgeon during surgery.

This task is solved by an eye surgical system of the kind referred to above wherein the computer unit is designed for the computation of the location of a patient eye provided outside of the center of the circular structure with at least one marking and the computer unit determines the location of the at least one marking with reference to the computed center by means of image processing via correlation with a comparison information.

The basis of the invention is the realization that, when imaging a patient eye on an image sensor, the limbus or the pupil edge of the eye define ring-shaped transition objects of brightness transitions which can be very precisely localized with a comparison to a comparison object configured as a ring filter. In addition, the invention is based on the realization that the position markings on a patient eye, which are introduced in advance of a cataract surgery on or in the immediate vicinity of the limbus circle in order to make visible a reference axis of the patient eye to the surgeon, are transition objects of brightness transitions which can be localized very precisely by comparison to a marking comparison object, by evaluating image brightness and/or by evaluating image colors. Here, it is shown that the localization of the transition objects is not falsified or only insignificantly falsified by surgical instruments which are moved for a short time on the patient eye.

To determine the location of the center of the circular structure, the computer unit correlates the image of the patient eye by means of image processing with comparison information. The computer unit computes for this purpose a quantity which is a measure for the degree of coincidence of the image of the patient eye and the comparison information. The comparison information comprises comparison objects which, in the computer unit, are placed over the image of the object plane. Preferably, the comparison objects are ring filters having an inner filter ring and an outer filter ring. The sign of the filter function $F_{r,(x_z,y_z)}(x,y)$ of the filter ring in the inner filter ring and in the outer filter ring is different.

Comprehensive experiments have shown that the position of, the limbus of a patient eye can be detected especially rapidly and reliably for a distance of the inner filter ring from the outer filter ring which corresponds to the dimension of two, three or four light-sensitive pixels of the electronic image sensor.

The computer unit determines the position of the center of the circular structure via convolution of the image of the object plane and the ring filters.

It is advantageous to provide an interface for the input of comparison information for the determination of the position of the center of the circular structure. Then, a rapid individual adjustment of the comparison information for a patient eye is possible.

Also for the determination of the position of the at least one marking in the patient eye, the computer unit correlates the image of the patient eye by means of image processing with a comparison information. As in the determination of the position of the center of the circular structure of the patient eye, the computer unit computes for this a quantity which is a measure for the degree of coincidence of the image of the patient eye and of the comparison information.

A comparison object likewise is suitable as comparison information for the determination of the position of the at least one marking in the patient eye, with the comparison object having a geometry which is adapted to the geometry of the marking. However, the color of a two-dimensional filter or a color of the at least one marking can also be applied as comparison information.

A region of a detected image of the patient eye is especially suitable as a comparison object. The position of the at least one marking can be detected especially reliably and rapidly in that this region is subjected to a color transformation F(R,G,B). The color transformation F(R,G,B) intensifies a known characteristic of the at least one marking of the patient eye, especially, a color of the marking.

It is advantageous to also provide this comparison information as an input in the eye surgery microscopy system.

An image processing in as short a computation time as possible is required in order to make possible a real time display of images of the patient eye. For shortening the computation time, the center of the circular structure and/or the angular position of the at least one marking is tracked by means of the computer unit after a corresponding initialization computation step.

It is advantageous here to provide an interface for the input of a tracking region. In this way, an operating person has influence on the magnitude of the data record which is the basis for the image processed in the computer unit.

In the eye surgery microscopy system, a display is preferably provided. A display for the target position of a toric intraocular lens and/or a display for the position and orientation of a patient eye is superposed on the detected image of the object plane. The display for the target position is defined by the center of the circular structure and by the position of at least one marking. The center of the circular structure is computed by the computer unit. As a display, an axis and/or an arrow and/or a cross marking is especially suitable.

An interface for the input of an intraocular lens target position and/or a data store for the storage of an intraocular lens target position is advantageously provided. Preferably, the control unit controls means for a movement compensated visualization of the patient eye with the information of the determined position of the circular structure. Optionally, it can also be provided that the computer unit controls means for a movement compensated visualization of the patient eye with the information of the determined position of the at least one marking.

In this way, a patient eye can be so visualized to the surgeon during surgery that disturbing flutter movements do not occur in the viewing image which are based on movements of the patient eye or unwanted movements of the eye surgery microscopy system.

A display is provided which is connected to the computer unit for the visualization of the image of the object plane detected by means of the image sensor and the computer unit transforms the detected image of the object plane in a display coordinate system wherein the coordinates of the center of the circular structure of the patient eye are invariant with respect to time. Because of the foregoing, the image of the patient eye can be visualized without translatory movements.

The computer unit can transform the detected image of the object plane also in a display coordinate system wherein the orientation of the displayed patient eye is invariant with respect to time. Then, the image of the patient eye can be visualized on the display rotatingly unmoved.

The movement compensated display of images makes possible especially that details of the images of the patient eye can be displayed at high magnification and can be examined by a viewing person since no image flutter occurs.

It is advantageous to provide a surgical microscope in the eye surgery microscopy system for the visualization of the patient eye and to configure the means for a movement compensated visualization of the patient eye as a drive for a movable microscopy system component assembly. The drive is driven in correspondence to the displacement of the image of the object plane on the image sensor. The microscopy system component assembly can, for example, be configured as an XY-coupling translatorily moving the microscopy system main objective. Especially, the eye surgery microscopy system can include a surgical microscope having a surgical microscope base body accommodated on a stand. The XY-coupling is provided between a stand arm and the surgical microscope base body.

It is advantageous to provide a filter stage for a time-dependent averaging of the computed position and/or orientation so that the surgical microscope is displaced without jolts and without rapid movements.

The invention further relates to a method for determining the position of a patient eye having a circular structure wherein the position of the center of the circular structure is determined by means of image processing via correlation with a first comparison information. Further, the invention relates to a method for determining the orientation of a patient eye having a circular structure which is provided with a marking outside of the center of the circular structure wherein the position of the marking is determined via correlation with a second comparison information. Based on the determination of the position of the center of the circular structure and the determined position of the marking, a coordinate system, which is stationary to the patient eye, can be referenced to a coordinate system which is stationary to the eye surgery microscopy system.

Furthermore, the invention relates to a computer program for carrying out this method.

The invention relates especially to an eye surgery microscopy system wherein the position and orientation of a patient eye, which has a circular structure, are determined with the eye being provided with a marking outside of the center of the circular structure in that the location of the center of the circular structure is computed by means of image processing via correlation with a first comparison information. Then, the position of the marking is determined by correlation with a second comparison information and then, based on the determined location of the center of the circular structure and the determined location of the marking, a coordinate system, which is stationary to the patient eye, is referenced to a coordinate system which is stationary to the eye surgery microscopy system.

For the movement compensated visualization of a patient eye, which has a circular structure, with the eye surgery microscopy system, the position of the center of the circular structure is continuously determined via correlation with a first comparison information and a displacement of the location of the center of the circular structure is detected and then the image is displaced on a visualization display in opposition to the detected displacement.

For the movement compensated visualization, the position of the marking can especially be detected by means of image processing via correlation with a second comparison information and then the image is shifted in a visualization display in opposition to the detected displacement.

BRIEF DESCRIPTION OF THE DRAWINGS

The invention will now be described with reference to the drawings wherein:

FIG. 10 shows an image of a patient eye, which is displayed on the video display screen of the microscopy system for eye surgery and with the patient eye being shown with an angular segment of a circle;

FIG. 11 shows two displays on the video display screen of the microscopy system for eye surgery; and, FIG. 12 shows a display on the video display screen of the eye surgery microscopy system with a magnified image representation.

DESCRIPTION OF THE PREFERRED EMBODIMENTS OF THE INVENTION

Figure 1:
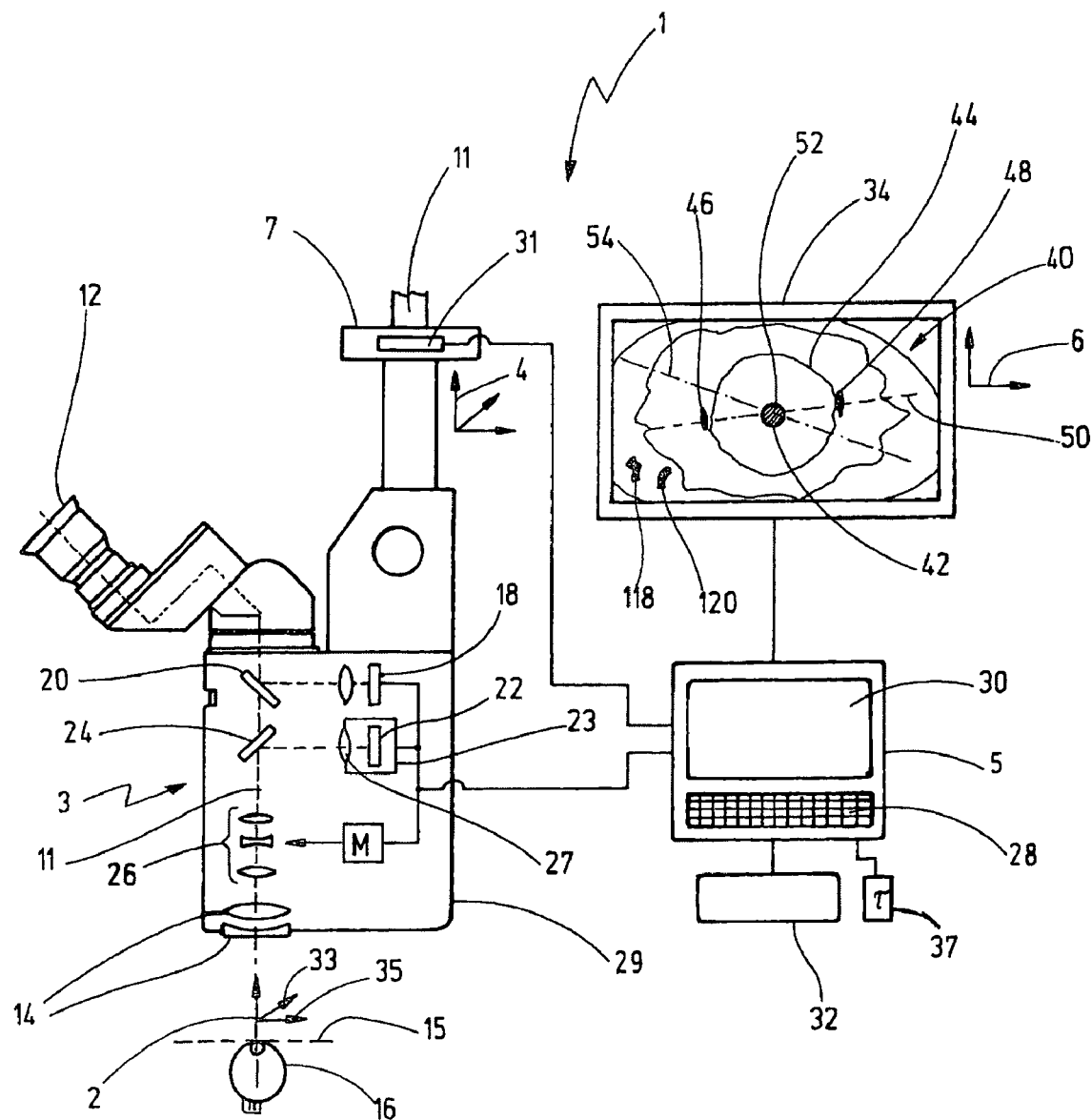
FIG. 1 shows a microscopy system for eye surgery with a video camera and a video display screen.

The eye surgery microscopy system 1 of FIG. 1 includes a surgical microscope 3 having a computer unit 5. The surgical microscope 3 has a surgical microscope base body 29. The surgical microscope 3 is accommodated with an XY-adjusting unit 7 on the arm 9 of a stand not shown further. A suitable XY-adjusting unit is, for example, described in DE 198 56 696 A1. The surgical microscope 3 permits a viewing person to view a patient eye 16 with magnification in an object plane 15 via a binocular viewing beam path 11 through a binocular viewer 12 and an imaging optic having a microscope main objective 14. The surgical microscope 3 has a unit for reflecting in data with a display 18 and a beam splitter 20. Further, a video camera 23 is integrated into the surgical microscope 3 and has a CCD-component as an image sensor 22. The CCD-component has light-sensitive pixels whose edge lengths are approximately 0.03 mm. The object image is supplied to the image sensor 22 via a beam splitter 24 in the viewing beam path 11 and via an imaging lens 27. The video camera 23 is a PAL-color camera. The camera makes available an RGB-image information with a red color channel (R), with a green color channel (G) and with a blue (B) color channel.

The surgical microscope 3 has a motor adjustable magnification system 26. The computer unit 5 is provided in the eye surgery system for controlling the surgical microscope 3. The computer unit 5 detects image data recorded with the image sensor 22 of the video camera 23 in order to further process the image data with a computer program. The computer unit 5 has input interface 28 in the form of a keypad and includes a display screen 30 which functions as an output interface. A data memory 32 is assigned to the computer unit 5.

The XY-adjusting unit 7 has a motor drive 31. This drive 31 is connected to the computer unit 5 via a control line. With the XY-adjusting unit 7, the surgical microscope 3 can be moved in translation parallel to the object plane 15 over the patient eye 16 in correspondence to the directions (33, 35). For the control of the drive 31, a filter stage 37 is assigned to the computer unit 5.

The computer unit 5 is connected to an external video image screen 34. In this way, image data, which is processed by the computer unit 5, can be displayed on the external video display screen 34 as well as in the unit for reflecting in data with the display screen 18 in the surgical microscope 3.

The video image screen 34 shows the image 40 of the patient eye 16 visualized with the eye surgery microscopy system 1. The patient eye 16 has a first circular structure 42 in the form of the pupil. A second circular structure 44 is formed by the limbus in the patient eye. The limbus identifies the transition between sclera and cornea in the patient eye. The pupil and the limbus have a center 52 disposed in the region of the lens of the patient eye 16. At the edge of the limbus, the patient eye is provided with a marking 46 and a marking 48. These markings (46, 48) are introduced into the patient eye 16 by means of a tincture which can be tolerated by the patient. For example, non-invasive ink is suitable as a tincture for the markings. The ink comprises a mixture of black carbon and a rapidly-drying binding agent such as polysaccharide alcohol or polyvinyl alcohol. The tincture can, however, also have a blue coloring. Such markings are applied in a patient's eye in advance of cataract surgery with a brush, pen or nozzle in order to establish a coordinate system 2 stationary to the patient's eye 16. The coordinate system 2 is defined by the center 52 of the pupil or limbus of the patient eye 16 and the markings (46, 48).

From the image information detected by the image sensor 22, the computer unit 5 computes the position of the center 52 of the circular structure 44 of the limbus as well as the position of the markings (46, 48) in a coordinate system 4 stationary to the eye surgery microscopy system 1.

In this way, reference can be made to the coordinate system 2, which is stationary to the patient eye 16, and to the coordinate system 4, which is stationary to the eye surgery microscopy system 1.

The computer unit 5 computes a connecting line 50 to the markings (46, 48) which is displayed on the video display screen 34. This connecting line 50 marks a stationary reference axis in the system of the patient eye 16. The connecting line 50 and the center 52 of the limbus or pupil fix a coordinate system 2 stationary to the patient eye 16.

The computer unit 5 references the coordinate system 2, which is stationary to the patient eye 16, and the coordinate system 4 which is stationary to the eye surgery microscopy system 1. The computer unit 5 then computes a target axis 54 from the patient data in the coordinate system 4 stationary to the eye surgery microscopy system 1. This target axis can be selectively displayed on the display 18 of the unit for reflecting in data and on the video image screen 34 via the computer unit 5. On this target axis 54, a surgeon can align a toric intraocular lens seated in the patient eye 16 during cataract surgery.

In the eye surgery microscopy system 1 of FIG. 1, a visualization of the patient eye 16 with a suitable target axis 54 is provided for a patient eye on the video display screen 34 in real time. That is, the parameters for the course of the target axis 54 have to be determined in real time. For this purpose, the computer unit 5 tracks the center of the circular structure of the limbus and the angular positions of the markings (46, 48) after a start position and a start orientation for the patient eye has been determined.

Figure 2:
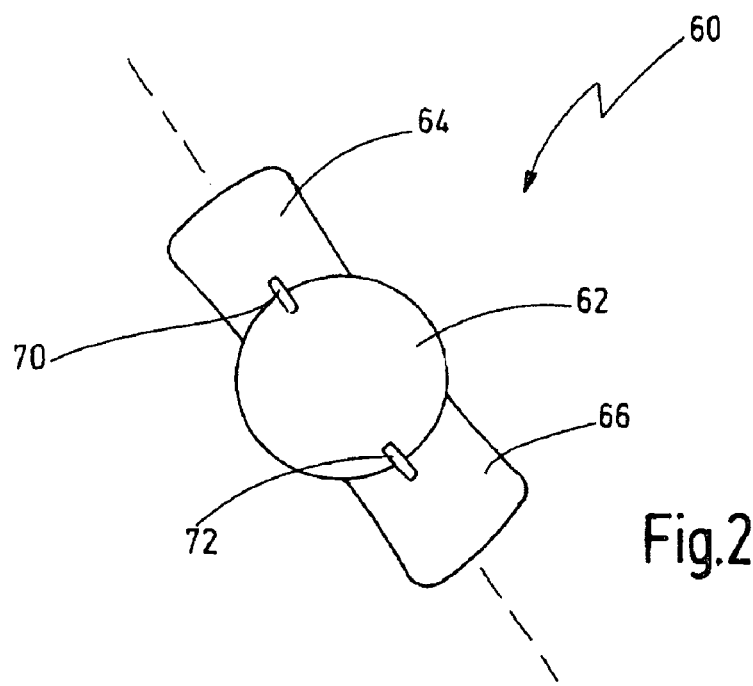
FIG. 2 shows a toric intraocular lens having position markings.

FIG. 2 shows a toric intraocular lens 60. The intraocular lens 60 has a lens body 62 having a torus geometry and includes holding sections (64, 66) which carry the lens body 62. Markings (70, 72) are provided on the holding sections (64, 66). These markings (70, 72) project into the lens body 62. The markings (70, 72) permit a surgeon during cataract surgery to align such a lens to the target axis 54 shown by means of the video image screen 34.

The position of the center 52 of the circular structure 44 of the limbus and the position of the markings (46, 48) of the patient eye 16 are determined in the computer unit 5 by image processing of the image information detected by the image sensor 22. In addition, the computer unit 5 computes the position of the center 52 of the circular structure of the limbus of the patient eye 16 in a first initialization computation step.

The first initialization computation step is described in detail on page 8, line 15, to page 10, line 20, of international patent application PCT/EP2008/068103 with reference to FIGS. 1 to 5. The subject matter of this application is therefore incorporated herein by reference in its entirety.

In a second initialization computation step, the angular position of the markings (46, 48) about the center 52 is determined with the computer unit 5.

After the first and second initialization computation steps, the position of the center 52 of the circular structure 44 of the limbus and the angular positions of the markings (46, 48) with reference to the center 52 are computed for shortening the computation time in a tracking mode.

A method for tracking, that is, tracking the center 52 of the circular structure 44 of the limbus is described in detail on page 9, line 21 to page 14, line 29, of international patent application PCT/EP2008/068104 with reference to FIGS. 1 to 5. The subject matter of this international patent application is therefore also incorporated completely herein by reference into this application.

In the tracking mode, the center 52 of the circular structure 44 of the limbus and the angular positions of the markings (46, 48) are tracked in correspondence to the movement of the patient eye 16.

Figure 3:
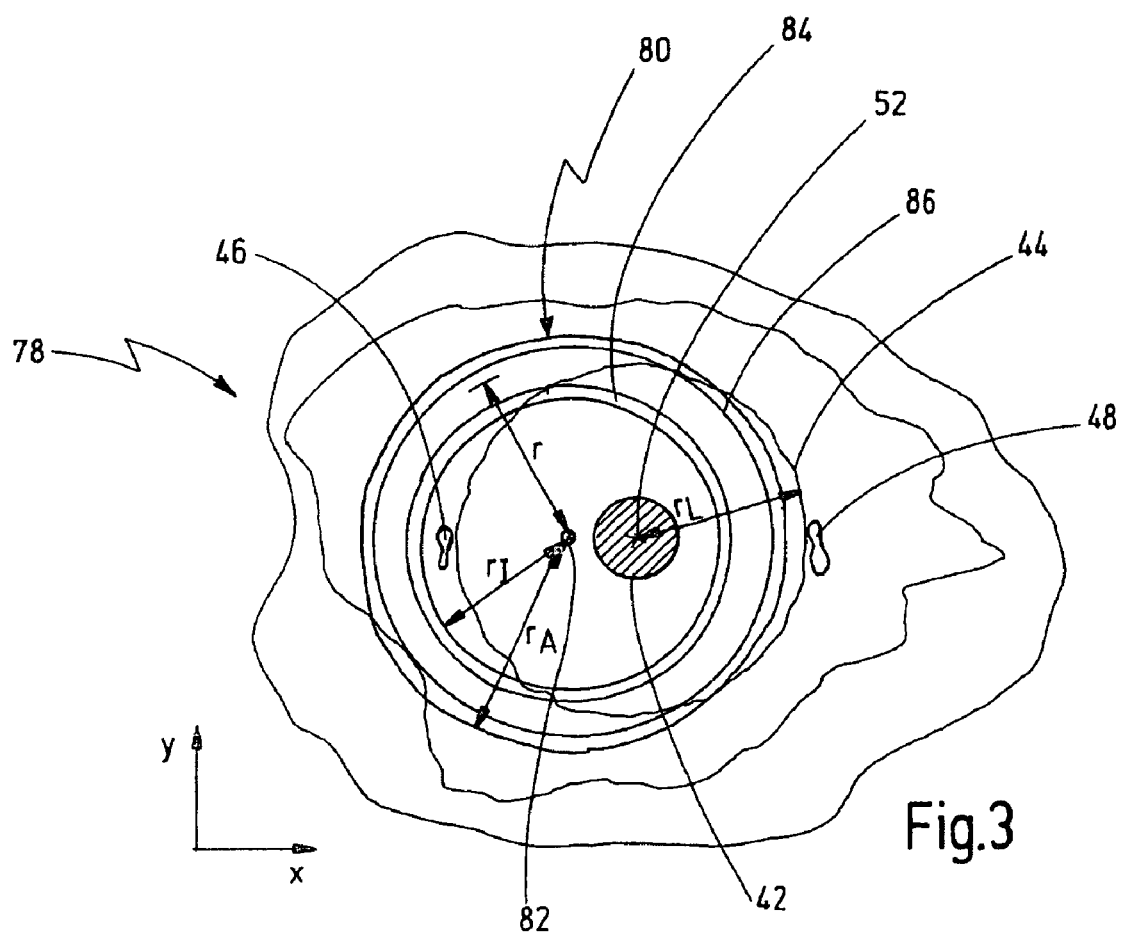
FIG. 3 shows an image of a patient eye with a comparison structure configured as a ring filter with the patient eye being shown on the video display screen of the eye surgery system.

An image 78 of the patient eye, which is detected by the image sensor 22, is shown in FIG. 3. In the first initialization computation step, the image 78 of the patient eye is correlated via filters with a plurality of comparison objects with a comparison information. The comparison objects are comparison structure filters which are placed over the image 78 in the context of an image processing by the computer unit 5.

A comparison structure filter 80, which is configured as a ring filter, is shown in FIG. 3. The ring filter 80 has a ring filter center 82 and includes an inner filter ring 84 and an outer filter ring 86. The inner filter ring 84 is arranged at a radial distance $r_I$ in the ring filter center 82 in a location $(x_z, y_z)$. The outer filter ring 86 is arranged centric to the inner filter ring 84 and is disposed at a radial distance $r_A$ from the filter center 82.

The filter function $$F_{r,(x_z,y_z)}(x,y)$$

of the ring filter 80 is characterized by the location $(x_z, y_z)$ of the ring filter center and the filter radius $$r := \tfrac{1}{2}\{r_A + r_I\}.$$

For the filter function $F_{r,(x_z,y_z)}(x,y)$ of the ring filter 80, the following applies:

$$F_{r,(x_z,y_z)}(x,y) = \begin{cases} -c & \text{for image points in the inner filter ring 84} \\ +c & \text{for image point in the outer filter ring 86} \end{cases}$$

The width of the inner filter ring 84 and of the outer filter ring 86 corresponds to the dimension of a light-sensitive pixel on the image sensor 22. The distance of the inner filter ring 84 from the outer filter ring 86 corresponds to the dimension of the two light-sensitive pixels on the image screen, that is, approximately 0.06 mm. This distance can, however, also correspond to the diameter of 3 or 4 light-sensitive pixels on the image sensor 22, that is, 0.09 mm or 0.12 mm. Comprehensive experiments have shown that, with this geometry of the filter rings (84, 86), the limbus of the patient eye can be especially reliably located. The diameter of the limbus is, on average, approximately 12 mm.

The filter function $F_{r,(x_z,y_z)}(x,y)$ is so standardized that the filtering of a gray area with a brightness distribution $I_g(x,y) = g$, that is, the convolution of the filter function with this brightness distribution yields the filter response $A\{F_{r,(x_z,y_z)}(x,y), I_g(x,y)\}$ wherein:

$$A\{F_{r,(x_z,y_z)}(x,y)\} = \iint dx' dy' F_{r,(x_z,y_z)}(x-x', y-y') I_g(x',y') = 0$$

Figure 4:
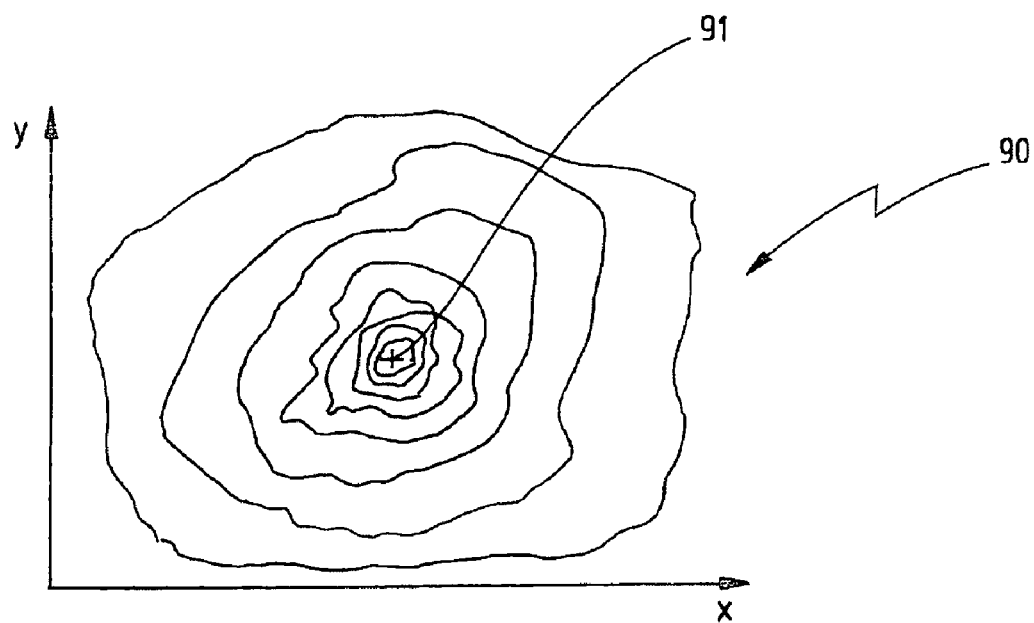
FIG. 4 is a graphic representation of the filter response with lines showing elevation for a plurality of ring filters placed upon the image of the patient eye.

In FIG. 4, the filter response $A\{F_{r,(x_z,y_z)}(x,y)\}$ is plotted for a constant ring filter radius r and for a plurality of positions $(x_z, y_z)$ of the ring filter center as elevation line profile 90 for the image of the patient eye shown in FIG. 3.

The filter response $A\{F_{r,(x_z,y_z)}(x,y)\}$ is a measure for the degree of matching of the image of the patient eye and of the comparison information in the form of a comparison structure filter configured as a ring filter.

The absolute magnitude of the filter response $A\{F_{r,(x_z,y_z)}(x,y)\}$ has a maximum $M_A(r)$ for the position of the filter shown in FIG. 3 wherein the ring filter center $(x_z, y_z)$ is disposed in the center of the circular structure 44 of the limbus of the patient eye at the location $(x_z, y_z)$. In FIG. 4, the maximum $M_A(r)$ is made recognizable by reference numeral 91. The magnitude of the maximum $M_A(r)$ is dependent upon how far the radius of the circular structure 44 of the limbus corresponds to the radius r of the ring filter.

Figure 5:
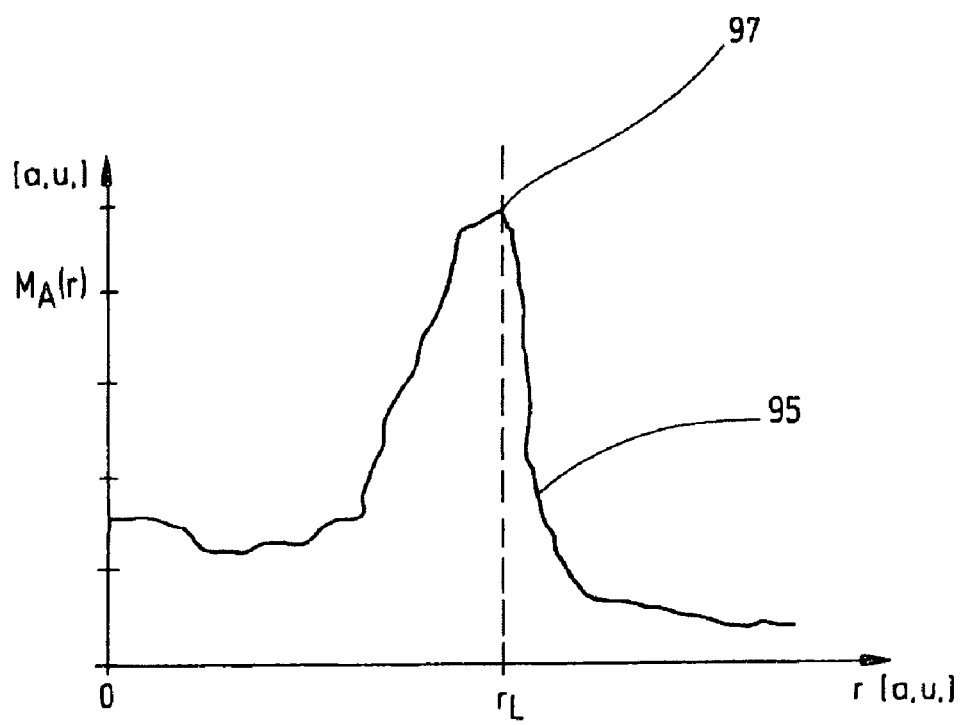
FIG. 5 is a graphic representation showing the dependency of a maximum filter response and a ring filter radius.

In FIG. 5, the dependency of a maximum 91 of FIG. 4 on the radius r of the ring filter is plotted as a curve 95. When the radius r of the ring filter, which is placed upon the image 78 of the patient eye, corresponds to the radius $r_L$ of the circular structure 44 of the limbus, the value $M_A(r_L)$ for the absolute magnitude of the maximum or minimum $M_A(r)$ of the filter response $A\{F_{r,(x_z,y_z)}(x,y)\}$ is a maximum at reference numeral 97.

The computer unit 5 selects that ring filter function for the image 78 of the patient eye from a plurality of ring filter functions for which the magnitude of the filter response is the greatest. From the position $(x_z, y_z)$ of the ring filter center for this filter function and the radius r of the ring filter, the position of the center 52 of the circularly-shaped structure of the limbus and the radius of this structure result.

For the determination of the position of the center of the circular structure 44 of the limbus of the patient eye, the computer unit 5 correlates the image of the object region, which is detected by the image sensor 22, with the ring-shaped comparison objects of different size. This is described in detail on page 3, line 12 to page 4, line 14 and page 5, line 9 to page 9, line 15, of international patent application PCT/EP2008/068104 and also in the international patent application PCT/EP2008/068103.

The correlation takes place by computing a suitable correlation function, preferably with a variation of the location, so that the correlation function is a function of the location variables. Here, the values of the image points of the image are computed with the values of the image points of the comparison object while the comparison object is moved over the image. The value of the correlation function is a measure for the coincidence of the image and the comparison object. For the maximum coincidence of image and comparison object, that is, when the characteristic feature of the comparison object and the sought for characteristic feature in the image are coincident, the value of the correlation function is a maximum.

The position of the center 52 of the circular structure 44 and the radius of the circular structure 44 are so determined as position and radius of that ring-shaped comparison object for which the magnitude of the value of the particular correlation function is a maximum.

Figure 6:
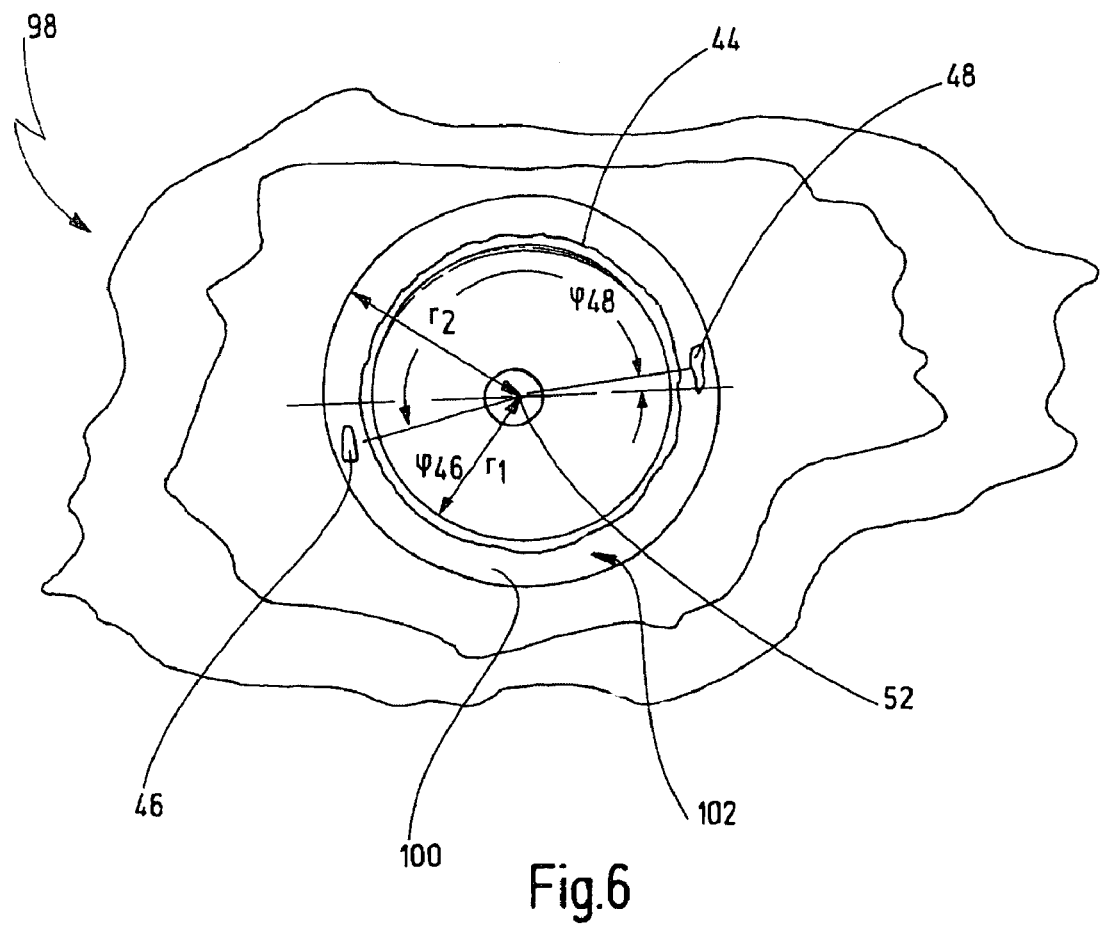
FIG. 6 shows the image of a patient eye which is shown on the video display screen of the eye surgery system and, in the patient eye, a circularly-shaped image detail is defined.

FIG. 6 shows the image 98 of the patient eye 16 for which, in a first initialization computation step, the radius of the circular structure 44 of the limbus and the position of the center 52 of the circular structure were computed. The image 98 is detected by the image sensor 22 of the eye surgery microscopy system 1.

To determine the position of the markings (46, 48) of the patient eye, a ring-shaped image detail 100, which is placed about the center 52 and in which the markings (46, 48) are found, is determined via an input interface 28 of the computer 5. The ring detail 100 has an inner radius $r_1$ and outer radius $r_2$. Alternatively, an image detail, which is matched to the computed radius $r_L$ of the limbus, can be defined based on experience values and which is stored in the data memory 32 of the computer unit 5.

Figure 7:
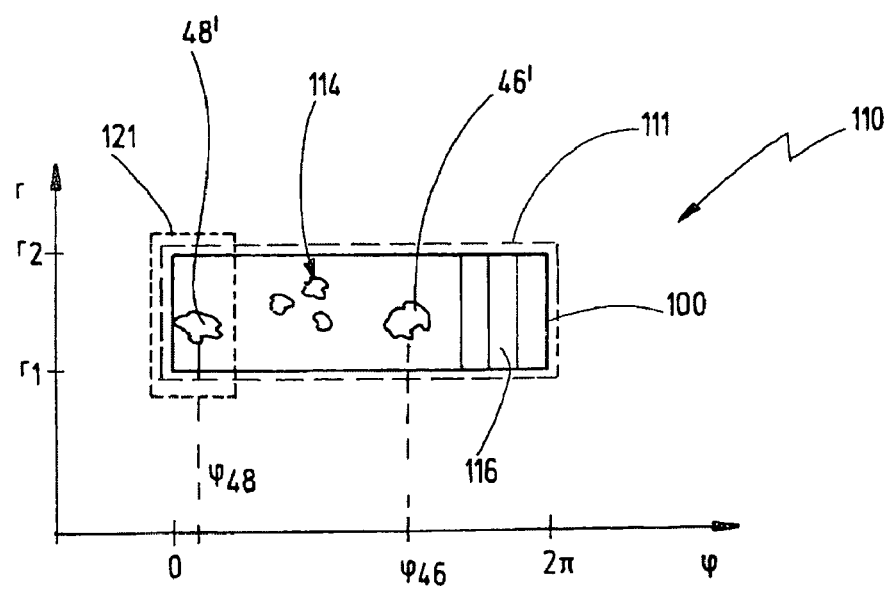
FIG. 7 shows a circularly-shaped image detail of FIG. 6 in a transformed coordinate system.

When the ring-shaped image detail 100 was determined, the computer unit 5 transforms the image points 102 in this image detail 100 into a two-dimensional polar coordinate system 110 shown in FIG. 7.

After converting the image points in this coordinate system, the angular positions ($\phi_{46}, \phi_{48}$) of the markings (46', 48') are determined via filtering with a two-dimensional filter 111, matched to the color of the markings, while forming threshold values and, if needed an area centroid determination. Here, the position of the markings (46', 48') is determined via computation of the filter response for the filter 111, that is, by correlation with the color of the two-dimensional filter as comparison information.

Alternatively to this, it is also possible to correlate the position of the markings (46', 48') while varying the location similar to the determination of the position of the center of the limbus with a plurality of comparison objects 114 in the image detail 100. Here, the comparison information is in the position and geometry of the comparison objects.

A further alternative for the determination of the angular position of the comparison object comprises a segmentation of the rectangle 92 in FIG. 7 into a plurality of part segments 116 with the rectangle corresponding to the image of the circularly-shaped image detail 100 in FIG. 6. Then, and with the computer unit 5, for example, via the criterion of the color of image points, the angular positions of the markings (46', 48') are determined. Here, the positions of the markings (46', 48') are determined by correlation with the color of the markings as comparison information.

It is noted that the localization of the markings (46, 48) in the patient eye 16 can also take place half automatically. It is, for example, possible that the operating person marks two positions on the video display screen 34 via the input interface 28 of the computer unit 5. Thereafter, in the close proximity of the two positions, the corresponding markings (46, 48) are sought after via the computer unit.

Alternatively hereto, it is also possible that an operating person recorrects located positions for the markings (46, 48) via an input at the input interface 28 of the computer unit 5.

Finally, a manual localization of the markings (46, 48) can be realized on the patient eye 16. For this purpose, it is provided in the eye surgery system 1 in FIG. 1 that an operating person can so displace two marking elements (118, 120), which are shown on the video display screen 34, via the input interface 28 of the computer unit 5 that these marking elements can be brought into coincidence with the positions of the marking elements (46, 48).

Furthermore, it is basically also possible to evaluate only one of the usually provided two markings (46, 48) for the localization of a reference axis of the patient eye. In this case, the reference axis is defined by the center 52 of the limbus circle and the position of this individual marking. It is noted that this is, however, only purposeful when the reference axis, which was fixed pre-operatively on the patient eye by two markings, runs approximately through the center of the limbus circle.

The information as to the angular positions of the markings (46, 48) in the image of the patient eye shown in FIG. 6 on the limbus circle is obtained in that a back transformation of the polar coordinates onto the circular structure 44 of the limbus is undertaken by means of the computer unit 5.

Figure 8:
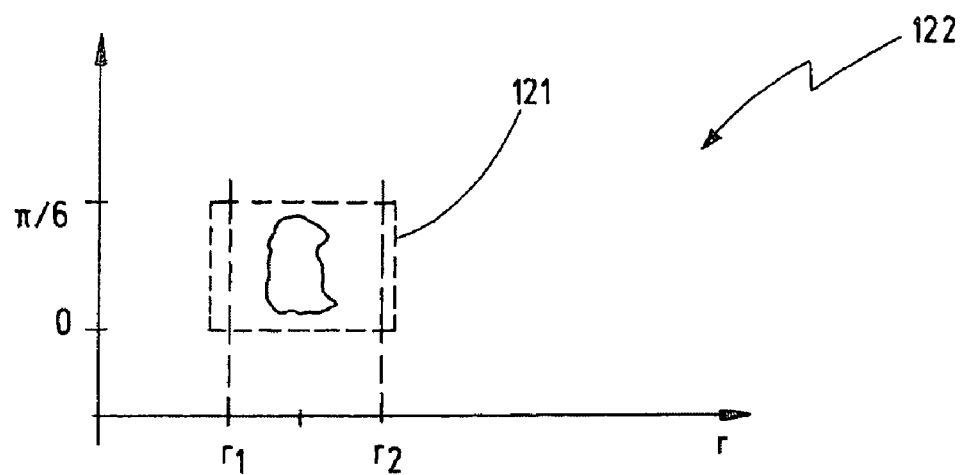
FIG. 8 shows a detail of FIG. 7 in a transformed coordinate system.

For the determination of the radial positions of the markings (46, 48) in the image 98 of the patient eye, which is shown in FIG. 6, on the circularly-shaped structure 44 of the limbus, it is advantageous to select an image detail 121 to each marking (46', 48') in FIG. 7 and to transform this image detail into a modified coordinate system 122 shown in FIG. 8. There, the x-axis and y-axis are exchanged with reference to the coordinate system 110 in FIG. 7.

The information as to the radial positions of the markings (46, 48) can be determined with computing methods via the coordinate system 110 by means of the computer unit 5. The computing methods correspond to the methods explained in FIG. 6 for the determination of the angular positions of the markings.

When the position of the center 52 of the circular structure 44 of the limbus of the patient eye and the radial positions of the markings (46, 48) are determined, the computer unit 5 determines the coordinate system 2 which is stationary to the patient eye 16. Thereafter, the coordinate system 2 is referenced to the coordinate system 4 of the eye surgery microscope system 1.

Figure 9:
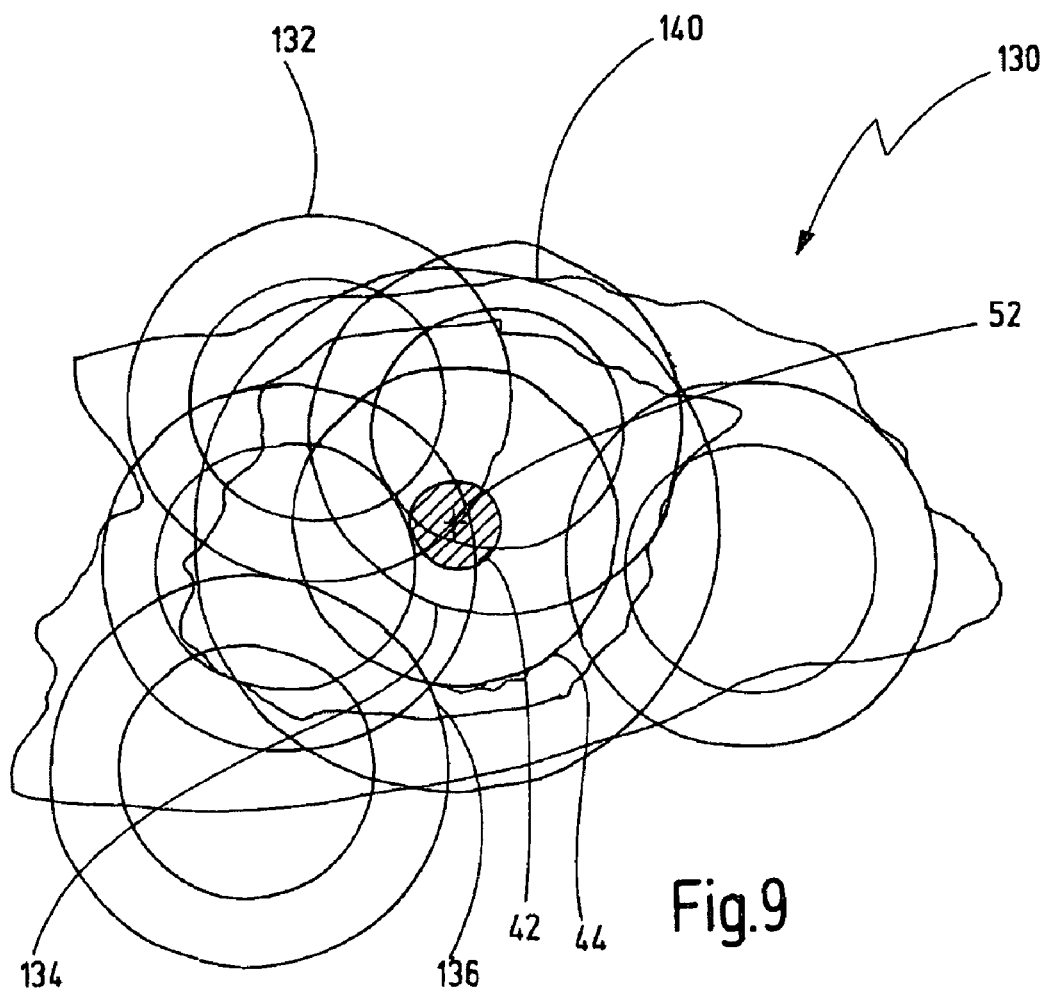
FIG. 9 shows the image of a patient eye, which is displayed on the video display screen of the eye surgery system with the patient eye being shown with several comparison structures configured as ring filters.

To track the position of the center 52 of the circular structure 44 of the limbus of the patient eye, which is shown in FIG. 9, each image 130 from an image sequence of the patient eye 16 detected by the image sensor 22 or selected individual images from an image sequence are again convoluted with a plurality of comparison structures (132, 134, 136,...) which are configured as ring filters. As filter radius r of the ring filter comparison structures (132, 134, 136,...), the radius $r_L$ of the circular structure 44 of the limbus is selected. This radius $r_L$ is determined in the first initialization step. The comparison structures lie in a tracking region determined by an image detail 140. The tracking region 140 is a circle 142 having a center corresponding to the center of the circular structure 44 of the limbus found in the first initialization computation step. The radius of the circle 142 can be inputted via the interface 28 of the computer unit 5. It is, however, advantageous to provide for the input of desired geometries of the tracking regions at the interface of the computer unit.

From the corresponding filter responses $A\{F_{r,(x_2,y_2)}(x,y)\}$, that filter response is determined from comparing the computed values whose magnitude forms the maximum. This maximum then corresponds, as explained with reference to FIG. 4, to that ring filter having a center which lies over the center of the limbus of the circular structure 44 of the patient eye.

For tracking the angular position of the patient eye 16, the following takes place: after the computation of the positions of the markings (46, 48) in the context of the second initialization computation step, marking-tracking regions are fixed and stored as comparison objects in the form of reference regions.

It is here also advantageous for the fixing of the tracking regions, to provide the possibility of the input via the interface 28 of the computer unit 5.

FIG. 10 shows the image 150 of a patient eye with a marking-tracking region 152 and a marking-tracking region 154. In these marking-tracking regions (152, 154) corresponding markings (46, 48) lie. The assumption that the angle positions ($\phi 46$, $\phi 48$) of the markings (46, 48) do not leave a specific angular region when the patient eye moves is the basis of the marking-tracking regions (152, 154).

Selected image details are cut out from the continuously detected images of the patient eye. These selected image details correspond to the reference regions, which were fixed in the second initialization computation step, but displaced by the translation of the patient eye detected with the position tracking.

The selected image details are then converted into such gray scale images which intensify in a targeted manner the known characteristics of the markings (46, 48):

When the markings (46, 48) of the patient eye are in a blue coloring, it is especially favorable to evaluate the green channel of the RGB color image of the patient eye made available by the video camera 23. Alternatively, it is possible to provide the color transformation $F(R,G,B):=B|G+B|R$ for the RGB image.

The reference regions (156, 158), which are computed and stored in the second initialization computation step, are subjected to the same transformation.

Thereafter, the selected image details are correlated with the corresponding reference regions. In the result of the computation, the position of the maximum is then determined. A rotation relative to the original axis position then results, for example, from a deviation of the position of the maximum from the center in the left direction which corresponds to the angle coordinate in the detailed image regions.

For the mentioned computation steps, it is advantageous to provide a coordinate transformation for the images of the patient eye which causes the marking-tracking regions (152, 154) to have a rectangular shape.

For the case wherein no or only slight rotational movements occur in a patient eye during cataract surgery, it is not absolutely necessary to track the angular axis of the patient eye. Here, it is then sufficient to localize the reference axis one time and thereafter to display the same at a constant angle position shifted by the translation of the eye detected during position tracking.

It is possible to provide several and possibly overlapping regions as tracking regions in lieu of one region per marking.

In this way, it is possible to track rotational movements of the eye over a wide angle region.

In the eye surgery system 1 of FIG. 1, the angular positions of the markings of the patient eye are visualized with a reference axis running through the center of the limbus. With the determination of the positions of the markings, the information as to the position of the limbus and the information as to the angular position of the patient eye in a coordinate system, which is stationary with reference to the eye surgery system, is present in the computer unit 5. For this reason, the alignment of a toric intraocular lens 60 in the patient eye can be visualized on the video display screen 34 via the target axis 54.

The target position of the toric intraocular lens 60 in the patient eye, that is, the course of the target axis 54 must, as a rule, be determined in advance of surgery and with reference to a reference axis defined with markings (46, 48).

The input interface 28 is provided in the computer unit 5 for inputting the course of the target axis. For the course of the target axis on a patient eye, it is, however, also possible to access a data record with patient data stored in the data memory 32 for the computer, unit 5.

The reference axis is usually so marked that the wide markings (46, 48) and the center of the circular structure 44 of the limbus circle lie approximately on a line. For this reason, it is not absolutely necessary to determine the positions of the markings in the radial direction. As a rule, it is sufficient to use the angular position projected approximately onto the limbus as the position in radial direction.

Finally, it is noted that also arrows, cross markings or even markings combined with circles can be provided for the display of the target position of a toric intraocular lens in a patient eye.

The eye surgery microscopy system 1 shown in FIG. 1 can be operated in a movement-compensation mode. In a movement-compensation mode, the computer unit 5 computes a corresponding displacement of the display on the video display screen 34 from the detected reference information as to the coordinate system 2, which is stationary to the patient eye 16, and with reference to the coordinate system 4 which is stationary to the eye surgery system 1. For this, the computer unit 5 transforms the detected image 40 of the object plane 15 in a display coordinate system 6 wherein the coordinates of the center 52 of the circular structure 44 of the patient eye 16 are invariant with respect to time. In this way, the center 52 of the circularly-shaped structure 44 of the limbus of the patient eye 16 can always be displayed in the center of the video display screen 34.

In FIG. 11, two corresponding displays (160, 170) of the video image for different positions of the patient eye 16 are imaged on the video display screen of the eye surgery microscopy system 1.

Here, a movement compensation can take place only based on a shift of the center 52 of the limbus of the patient eye 16 or also a compensation for the rotary movements of the eye which can be detected because of the markings (46, 48).

Figure 12:
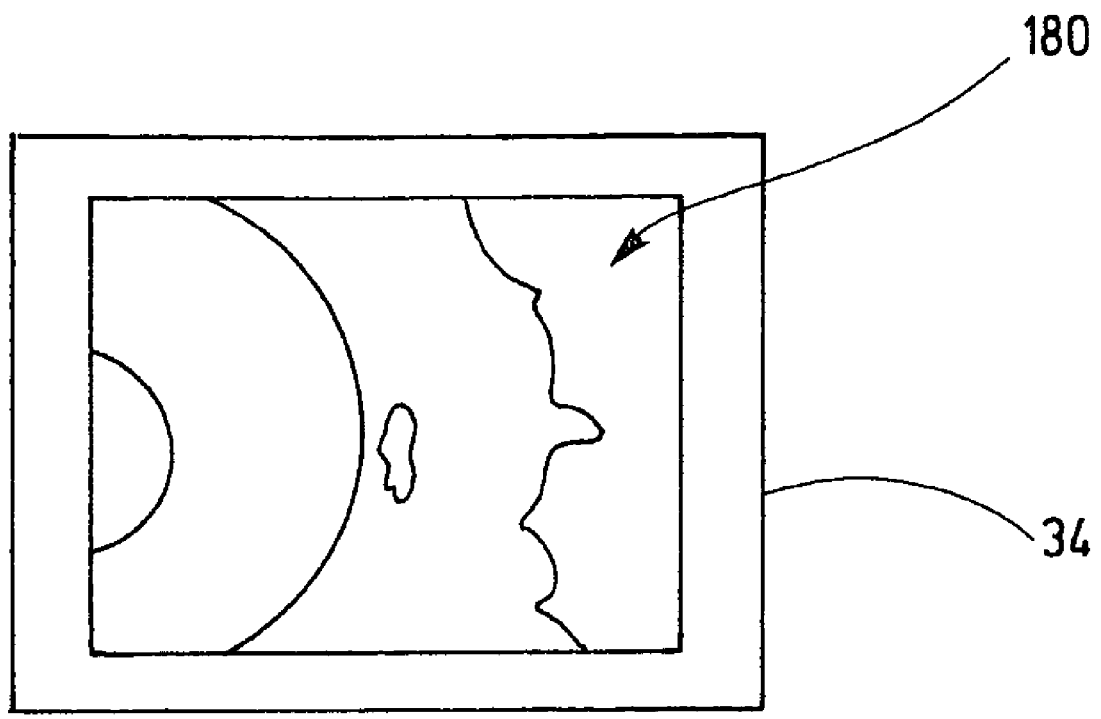

As shown in FIG. 12, the operation of the eye surgery microscopy system 1 in the mode for movement compensation makes possible especially the display of greatly magnified details 180 of real time images of the patient eye 16 which do not flutter. For this purpose, it is advantageous when each image is subjected to a corresponding image processing in the computer unit 5. Each image is detected with the video camera 23 in the surgical microscope 3. By utilizing PAL-video standards, this, however, makes necessary an image processing in time intervals of 40 ms. If only details from a video image sequence are subjected to image processing, that is, only each second or even only each fourth image of a corresponding image sequence, then it is accepted that the display appears shaky on the video display screen.

Alternatively, or in addition, the eye surgery microscopy system 1 in FIG. 1 can also be operated in a movement compensation mode wherein the relative movement of the coordinate system 2, which is stationary to the patient eye, and the coordinate system 4, which is stationary to the eye surgery system 1, can be compensated by driving the motor drive 31 of the XY-coupling. Since high frequency displacement movements can be perceived as disturbing by an operating person, the filter stage 37 is provided for the computer unit 5 in order to filter out corresponding high frequency relative movements.

In summary, the following is pertinent: the invention relates to an eye surgery microscopy system 1 having an imaging optic (14, 11) for the generation of the image of an object plane 15 and having an electronic image sensor 22, which detects the image of the object plane 15 and which is connected to a computer unit 5 for computing the position of the center of a circular structure 44 of a patient eye 16. The computer unit 5 is designed for the computation of the position of a patient eye 16 outside of the center 52 of the circular structure 44 having at least one marking (46, 48). The computer unit determines the position of the at least one marking (46, 48) with reference to the computer center 52 by means of image processing via correlation with a comparison information.

It is understood that the foregoing description is that of the preferred embodiments of the invention and that various changes and modifications may be made thereto without departing from the spirit and scope of the invention as defined in the appended claims.

What is claimed is:

1. An eye surgery microscopy system comprising:
   an imaging optic for generating an image of an object plane;
   an electronic image sensor for detecting said image of the object plane;
   a computer unit for computing the position of the center of a circular structure of a patient eye provided with at least one marking;
   said computer unit being further adapted to compute the position of the center of said circular structure by utilizing image processing via correlation with comparison information;
   said image sensor being connected to said computer unit;
   a plurality of comparison objects which, in said computer unit, are placed over said image of said object plane;
   each of said comparison objects being configured as a ring filter having an inner filter ring and an outer filter ring;
   said ring filter defining a filter function $F_{r,(x_z,y_z)}(x,y)$ having respectively different signs in said inner and outer filter rings;
   said computer unit being further adapted to determine said position of said center of said circular structure from values of filter responses of said ring filter determined from convoluting said image of said object plane and said filter function $F_{r,(x_z,y_z)}(x,y)$, wherein said computer unit is adapted to determine the position of the at least one marking disposed outside of the center of said circular structure via correlation with a marking-comparison information; and,
   a display and the display superposing on the image of the object plane at least one indicator for the target position of a toric intraocular lens and/or an indicator for the position and orientation of a patient eye, the indicator being defined by the center of the circular structure, which is computed by the computer unit, and by the position of the at least one marking.

2. The eye surgery microscopy system of claim 1, wherein said computer unit is adapted to determine the position of the center of said circular structure by determining a maximum of the magnitude of said values of said filter responses determined via convolution of said image of said object plane and the filter function of said ring filter.

3. The eye surgery microscopy system of claim 1, wherein said inner filter ring and said outer filter ring are separated by a distance corresponding to a dimension of two, three or four light-sensitive pixels of said electronic image sensor.

4. The eye surgery microscopy system of claim 1, further comprising an interface for inputting the comparison information for the determination of the position of the center of the circular structure.

5. The eye surgery microscopy system of claim 1, wherein the marking-comparison information for the determination of the position of the at least one marking is a comparison object.

6. The eye surgery microscopy system of claim 5, wherein a region of a detected image of the patient eye is provided as a comparison object.

7. The eye surgery microscopy system of claim 6, wherein said region is subjected to a color transformation F(R,G,B) which intensifies a known characteristic of the at least one marking of the patient eye.

8. The eye surgery microscopy system of claim 7, wherein the color transformation F(R,G,B) intensifies the color of the marking.

9. The eye surgery microscopy system of claim 1, wherein the comparison information is the color of a two-dimensional filter and/or a color of the at least one marking.

10. The eye surgery microscopy system of claim 1, further comprising an interface for inputting the comparison information for the determination of the position of the at least one marking.

11. The eye surgery microscopy system of claim 1, wherein said computer unit tracks the center of the circular structure and/or the angular position of the at least one marking for shortening computation time.

12. The eye surgery microscopy system of claim 11, further comprising an interface for inputting a tracking region.

13. The eye surgery microscopy system of claim 1, wherein the indicator is an axis and/or an arrow and/or a cross marking.

14. The eye surgery microscopy system of claim 1, further comprising an interface for the input of an intraocular lens target position and/or a data memory for the storage of an intraocular target position.

15. The eye surgery microscopy system of claim 1, wherein said computer unit controls means for a movement compensated visualization of the patient eye with the information of the determined position of the circular structure.

16. The eye surgery microscopy system of claim 15, wherein, for the visualization of the image of the object plane, which is detected by the image sensor, a display is provided which is connected to the computer unit; and, said computer unit transforms the detected image of the object plane into a display coordinate system wherein the coordinates of the center of the circular structure of the patient eye are invariant with respect to time in order to cause the image of the patient eye to appear translatorily unmoved.

17. The eye surgery microscopy system of claim 16, wherein said computer unit transforms the detected image of the object plane in a display coordinate system wherein the orientation of the patient eye is invariant with respect to time in order to cause the image of the patient eye to appear rotatingly unmoved.

18. The eye surgery microscopy system of claim 16, wherein the display visualizes details of the image of the object plane with magnification.

19. The eye surgery microscopy system of claim 15, further comprising a filter stage for the time averaging of the computed position and/or orientation.

20. The eye surgery microscopy system of claim 1, wherein the computer unit controls means for a movement compensated visualization of the patient eye with the information of the determined position of the at least one marking.

21. The eye surgery microscopy system of claim 20, further comprising a surgical microscope for the visualization of the patient eye;
wherein the means for a movement compensated visualization of the patient eye includes a drive for a movable microscopy system component assembly; and,
the drive being driven in correspondence to the displacement of the image of the object plane on said image sensor.

22. The eye surgery microscopy system of claim 21, wherein the microscopy system component assembly is an XY-coupling which translatorily moves the microscopy system main objective.

23. The eye surgery microscopy system of claim 22, wherein said eye surgery microscopy system includes a surgical microscope having a surgical microscope base body accommodated on a stand; and, the XY-coupling is provided between a stand arm and the surgical microscope base body.

24. The eye surgery microscopy system of claim 1, further comprising a surgical microscope defining a viewing beam path; said imaging optic disposed in said viewing beam path of said surgical microscope; and, a unit for reflecting the superposed image of the object plane into said viewing beam path of the surgical microscope.

25. A method for determining the position of a patient eye provided with at least one marking, the method comprising the steps of:
detecting an image of the patient eye with an electronic image sensor;
determining the position of the center of a circular structure of the patient eye utilizing image processing in a computer unit by correlating with comparison information defined by comparison objects;
in the computer unit, placing said comparison objects over the image of the object plane;
configuring said comparison objects as ring filters with each ring filter including an inner filter ring and an outer filter ring;
configuring said comparison objects as ring filters defining a filter function $F_{r,(x_2,y_2)}(x,y)$ with each ring filter including an inner filter ring and an outer filter ring and said filter function having different signs in said inner and outer filter rings;
in the computer unit, determining the position of the center of the circular structure from the values of filter responses of the ring filter determined by convolution of the image of the object plane and the filter function of the ring filters;
determining the position of the at least one marking disposed outside of the center of said circular structure via correlation with a marking-comparison information; and,
superposing on the image of the object plane at least one indicator for the target position of a toric intraocular lens and/or an indicator for the position and orientation of a patient eye, the indicator being defined by the center of the circular structure, which is computed by the computer unit, and by the position of the at least one marking.

26. The method of claim 25, wherein, in the computer unit, the position of a marking of the patient eye, which lies outside of the center of the circular structure, is determined by correlation with a marking-comparison information.

27. The method of claim 25, wherein the computer unit determines the position of the center of the circular structure by determining a maximum of the magnitude of said values of said filter responses determined via convolution of the image of the object plane and the filter function of the ring filter.

28. The method of claim 25, wherein the position of the center of the circular structure of the patient eye is continuously determined in the computer unit to detect a displacement of the patient eye; and, the image of the patient eye is displaced on a visualization display in opposition to the detected displacement of the center of the circular structure of the patient eye.

29. The method of claim 25, wherein a marking of the patient eye outside of the center of the circular structure of the patient eye is continuously determined to detect a displacement of the patient eye; and, the image of the patient eye is displaced in opposition to the detected displacement on a visualization display.

30. A computer program for controlling a computer unit in an eye microscopy system for carrying out a method according to claim 25.

31. An eye surgery microscopy system comprising:
an imaging optic for generating an image of an object plane;
an electronic image sensor for detecting said image of the object plane;
a computer unit for computing the position of the center of a circular structure of a patient eye;
said computer unit being adapted to compute the position of the center of said circular structure;
said image sensor being connected to said computer unit;
said computer unit being adapted for computing the position of at least one marking outside of the center of the circular structure with the patient eye being provided with at least one marking;
said computer unit being further adapted to determine the position of the at least one marking with reference to the computed center utilizing image processing via correlation with a comparison information wherein said computer unit is adapted to determine the position of the at least one marking disposed outside of the center of said circular structure via correlation with a marking-comparison information; and,
a display and the display superposing on the image of the object plane at least one indicator for the target position of a toric intraocular lens and/or an indicator for the position and orientation of a patient eye, the indicator being defined by the center of the circular structure, which is computed by the computer unit, and by the position of the at least one marking.

32. The eye surgery microscopy system of claim 31, further comprising a surgical microscope defining a viewing beam path; said imaging optic disposed in said viewing beam path of said surgical microscope; and, a unit for reflecting the superposed image of the object plane into said viewing beam path of the surgical microscope.

33. A method for determining the orientation of a patient eye comprising the steps of:
- providing the patient eye with a marking lying outside of the center of a circular structure;
- determining the position of the marking via correlation with a second comparison information;
- determining the position of the at least one marking disposed outside of the center of said circular structure via correlation with a marking-comparison information; and,
- superposing on an image of the patient eye generated with an imaging optic at least one indicator for the target position of a toric intraocular lens and/or an indicator for the position and orientation of a patient eye, the indicator being defined by the center of the circular structure, which is computed by a computer unit, and by the position of the at least one marking.

* * * * *

UNITED STATES PATENT AND TRADEMARK OFFICE
CERTIFICATE OF CORRECTION

PATENT NO.        : 8,308,298 B2
APPLICATION NO.   : 12/801780
DATED             : November 13, 2012
INVENTOR(S)       : Thomas Schuhrke et al.

Page 1 of 1

It is certified that error appears in the above-identified patent and that said Letters Patent is hereby corrected as shown below:

In the Specifications:

In Column 2:
Line 63: delete "of," and substitute -- of -- therefor.

In Column 8:

Line 15: delete "
$$F_{r,(x_z,y_z)}(x,y) = \begin{cases} +c & \\ -c \text{ for image points in the inner filter ring 84} \\ \text{for image point in the outer filter ring 86} \end{cases}$$
"

and substitute --
$$F_{r,(x_z,y_z)}(x,y) = \begin{cases} +c \text{ for image point in the outer filter ring 86} \\ -c \text{ for image point in the inner filter ring 84} \end{cases}$$
-- therefor.

Line 35: delete
"
$$A\{F_{r,(x_z,y_z)}(x,y)\} = \int\int dx'\,dy'\, F_{r(x_z,y_z)}(x-x', y-y')I_g(x',y') = 0$$
"
and
substitute
--
$$A\{F_{r,(x_z,y_z)}(x,y), I_g(x,y)\} = \int\int dx'\,dy'\, F_{r,(x_z,y_z)}(x-x', y-y')I_g(x',y') = 0$$
--.

Signed and Sealed this
Twenty-third Day of April, 2013

Teresa Stanek Rea
*Acting Director of the United States Patent and Trademark Office*